United States Patent [19]

De Haan et al.

[11] Patent Number: 4,708,874

[45] Date of Patent: Nov. 24, 1987

[54] DEVICES FOR THE CONTROLLED RELEASE OF ACTIVE SUBSTANCES, AS WELL AS PROCESS FOR THE PREPARATION THEREOF

[75] Inventors: Pieter De Haan, Groningen; Coenraad F. Lerk, Peize; Adelbert J. M. Schoonen, Groningen, all of Netherlands

[73] Assignee: Rijksuniversiteit Groningen, Groningen, Netherlands

[21] Appl. No.: 838,248

[22] Filed: Mar. 10, 1986

[30] Foreign Application Priority Data

Mar. 13, 1985 [NL] Netherlands ..................... 8500724

[51] Int. Cl.⁴ .............................................. A61K 9/52
[52] U.S. Cl. ...................................... 424/470; 427/3; 514/965; 523/122
[58] Field of Search ................ 424/20, 21, 22, 470; 514/965; 427/3; 523/122

[56] References Cited

U.S. PATENT DOCUMENTS

| | | | |
|---|---|---|---|
| 2,793,979 | 5/1957 | Svedres | 167/82 |
| 2,996,431 | 8/1961 | Barry | 427/3 |
| 3,119,742 | 1/1964 | Heimlich et al. | 424/20 |
| 3,166,476 | 1/1965 | Lowey | 424/21 |
| 3,634,584 | 1/1972 | Poole | 424/21 |
| 3,965,256 | 6/1976 | Leslie | 424/22 |
| 4,139,589 | 2/1979 | Beringer et al. | 427/3 |
| 4,193,985 | 3/1980 | Bechgaard et al. | 424/22 |
| 4,210,139 | 7/1980 | Higuchi | 128/260 |
| 4,235,870 | 11/1980 | Leslie | 424/22 |
| 4,415,547 | 11/1983 | Yu et al. | 424/20 |
| 4,454,108 | 6/1984 | Iida et al. | 424/20 |
| 4,572,833 | 2/1986 | Pedersen et al. | 427/3 |
| 4,574,080 | 3/1986 | Roswall et al. | 427/3 |
| 4,610,870 | 9/1986 | Jain et al. | 424/21 |

FOREIGN PATENT DOCUMENTS 829450 5/1975 Belgium .
2749745 3/1979 Fed. Rep. of Germany .
3218150 11/1983 Fed. Rep. of Germany .
55-153715 2/1981 Japan .
6907794 11/1969 Netherlands .
7207486 12/1972 Netherlands .
2103486 2/1983 United Kingdom .

OTHER PUBLICATIONS

Chemical Abstracts, vol. 95, No. 24, Dec. 1981, p. 370, Abstract 95: 209556s.
Chemical Abstracts, vol. 87, No. 24, Dec. 1977, p. 308, Abstract 87: 189398w.
Chemical Abstracts, vol. 90, No. 10, Mar. 1979, p. 280, Abstract 90: 76502u.
Chemical Abstracts, vol. 77, No. 6, Aug. 1972, p. 326, Abstract 77: 39139s.
Die Pharmazie, vol. 32 (Dec. 1977), pp. 771–777.
Drug Design, Ariens, vol. IV (1973), pp. 38–73, Academic Press, New York, N.Y.

Primary Examiner—Ronald W. Griffin
Attorney, Agent, or Firm—Dennison, Meserole, Pollack & Scheiner

[57] ABSTRACT

The invention relates to a device for the controlled release of one or more active ingredients to a liquid, particularly a controlled release pharmaceutical tablet obtained by compressing a mixture of two granulates in a weight ratio of 30:70 to 70:30, said granulates having particle sizes of 0.4–2.0 mm. One of the granulates, the restraining phase granulate, comprises one or more active ingredients dispersed in a matrix of an insoluble substance, and the other granulate, the housing phase granulate, comprises a soluble material and a penetration rate limiting material, one material optionally having both functions. In the compressed device, the granulates form two distinct phases, each of which is continuous. The housing phase fills large continuous pores in the restraining phase. A zero-order release rate can be obtained with the devices.

33 Claims, 9 Drawing Figures fig-1 fig-2 fig-3 fig-4 fig-5 fig-6

Fig-7

Fig-8

DEVICES FOR THE CONTROLLED RELEASE OF ACTIVE SUBSTANCES, AS WELL AS PROCESS FOR THE PREPARATION THEREOF

The invention relates to solid devices slowly releasing one or more active components when the devices are contacted with a liquid. The invention provides compositions for controlled release of drugs or nutrients, which compositions are particularly intended for administration via the gastro-intestinal tract and, therefore, the invention is particularly directed to pharmaceutical compositions. The pharmaceutical compositions do not only comprise compositions for oral administration, but also e.g. suppositories and implants. The devices according to the invention are also applicable in other fields, such as in agriculture, for example for the slow and uniform release of fertilizers, and in biotechnology, for example for the controlled release of nutrients.

Awareness of the importance of controlled release formulations is increasing in medicine. Especially with drugs having a relatively short half-life and administered orally, maintenance of therapeutically active blood-levels during an extended period of time often may be obtained in practice with such compositions only. Additionally, the use of such compositions allows limitation of the occurence of undesirable peak concentrations and increase of patient compliance because the drug has to be taken less frequently.

In general, a pharmaceutical composition should be capable of presenting the drug in an absorbable form to the absorbing surface. In the particular case of a composition for oral administration releasing the drug at a controlled rate, the composition should release continuously the drug contained therein within the period of time which is available for absorption. After oral administration, the total gastro-intestinal transit time (in the normal human: about 8 hours) puts a limit to the release period, but with certain drugs which can only be absorbed in parts of the gastro-intestinal tract, this period may be shorter. With a drug which cannot or should not be absorbed in the stomach, a lag time, before drug-release begins, may be desirable. Normally, a linear drug release (zero-order) after the beginning of the release is desirable.

It will be clear that no general formulation can be given which in all cases meets exactly the requirements, since all of the components present, including the drug, and its concentration, determine the ultimate result. However, the invention provides a general principle allowing the preparation of controlled release compositions of one or more active substances which meet the above-mentioned requirements.

Compositions releasing an active substance with a controlled release rate have been described before. W. A. Ritschel describes in Drug Design, Ed. E. J. Ariens, Volume IV, pages 38–73 (1972) nine different principles relating to the controlled release of active substances from usual capsules, pills and tablets, while recently the new principle of an osmotic device has been added to the arsenal of compositions showing controlled release (U.S. Pat. No. 4,210,139). The large number of available principles would allow the conclusion that none of these is free of shortcomings. For example, most of the compositions cannot guarantee zero-order release, some are only applicable to hydrophylic or to lipophylic drugs, some depend on intestinal enzymes or on the physical effects of the intestinal motility or are sensitive to pH, some are prone to losing their special characteristics or even to becoming dangerous after being broken (for example by mastication), and the preparation of many of the compositions is very expensive.

According to the invention a new principle of sustained release compositions is introduced, which compositions, in principle, do not show the above-mentioned shortcomings and further have the advantages described below.

The devices according to the invention comprise two continuous phases and are obtained by compressing a mixture of two different granulations. Controlled-release formulations consisting of more than one type of granulation have also been described before.

Belgian patent specification No. 829450 describes a process for preparing slow release tablets in which the active ingredient is incorporated in a granulate containing a water-insoluble wax-like material, which granulate is mixed with a second granulate easily decomposable in the gastro-intestinal tract due to the presence of soluble binders and disintegrating agents. The amounts of the granulates in the mixture are chosen in such a way that the first-mentioned, active granulate, after compression of the mixture, will be present as separate nuclei in the mass of the second granulate. A zero order release rate cannot be obtained with these tablets since the slow release granulate particles will be liberated relatively easily in the gastro-intestinal tract and then will release the drug in a decreasing rate.

British patent application No. 2,103,486 relates to formulations comprising quick-acting and slow-acting granules. The quick-acting granules consist of granule nuclei coated with active ingredients, and the slow-acting granules are obtained by providing the quick-acting granules with a coating of an enteric material.

U.S. Pat. No. 3,965,256 describes a slow-release pharmaceutical tablet comprising a drug, and a slow-release composition comprising 2 to 4 parts of a fatty alcohol ROH in which R is alkyl of 8–18 carbon atoms and/or cetostearyl alcohol, and one part of a hydrated hydroxymethyl, hydroxyethyl or hydroxypropyl cellulose or mixtures thereof, which tablet is prepared by granulating the fatty alcohol, granulating the hydrated hydroxyalkyl cellulose compound, blending the drug with one of the granulates or with mixtures thereof, drying the blend of granules and granulating the blend, and compressing the granules admixed with a sufficient quantity of a tablet diluent. The slow release composition is present in an amount of 20% of the total weight of the tablet. These tablets will not comprise two distinct phases.

Compositions comprising a non-sustained release granulation and a sustained-release granulation containing fatty material resistant to disintegration and slowly dispersible in the gastro-intestinal tract are described in U.S. Pat. No. 2,793,979. The sustained-release granulate is prepared by using as a granulation liquid an aqueous solution of a water-soluble binder, such as a soluble sugar, gelatin or a natural plant hydrocolloid. After compression of the mixture of non-sustained release granules and sustained-release granules, the sustained release granules will not form a continuous phase due to the presence of the water-soluble granulation agent. When in use, the tablet breaks down into a large number of individual time delay particles containing embedded medicament. German Offenlegungsschrift No. 3218150 discloses prolonged release formulations comprising microporous polymer powder or granulate loaded with active substance and dispersed in a degradable polymer matrix. A composition which comprises three types of granulations is described in German Offenlegungsschrift No. 2,749,745. The granulates have different release rates which, together, result in a desired release pattern. The release pattern of one granulate is not influenced by another granulate. The three granulates are preferably filled into capsules, but may also be compressed into tablets.

In "Die Pharmazie" 32, 771-777 (1977) a tablet is described which is obtained by compressing a retarding granulate and an easily soluble granulate. The retarding substance in the retarding granulate is an acrylic acid-/alkyl acrylate copolymer which is combined with an acidic substance. As soon as the tablet leaves the stomach the polymer forms a gel barrier which is intended to retard drug release. The tablet disintegrates completely in the gastro-intestinal tract due to dissolution of the polymer in the intestine after release of the acidic substance.

The devices according to the invention comprise two different phases. The first phase, further called the housing phase, is characterized by the presence of a liquid-soluble material and of a penetration rate limiting material (if desired, one material may have both functions). The other phase, further called the restraining phase, is characterized by the presence of one or more substances which are insoluble in the extracting liquids. In the devices, each of the two phases is continuous, that is to say, the restraining phase forms a continuous phase within the housing phase, and the housing phase forms a continuous phase within the restraining phase, so that the housing phase can be considered to fill large continuous pores within the restraining phase.

The device according to the invention for the controlled release of one or more active ingredients to a liquid is a shaped article obtained by compressing a mixture of two granulates in a weight ratio of 30:70 to 70:30, said granulates having particle sizes of 0.4–2.0 mm, one granulate which is called the restraining phase granulate, comprising one or more active ingredients dispersed in a continuous matrix comprising one or more substances which are insoluble in the liquid, and the other granulate which is called the housing phase granulate, comprising a liquid-soluble material, and a penetration rate limiting material, one material optionally having both functions.

The ingredients of the restraining phase granulate are selected in such a way that, in the device, the restraining phase will form a coherent matrix in which the active ingredient is dispersed. The matrix should retain its shape and should not substantially swell at least during the greater part of the release period.

Suitable liquid-insoluble materials which may be incorporated in the restraining phase are insoluble acrylic resins, cellulose derivatives, such as alkylcelluloses (for example ethylcellulose), other polymers such as polyvinyl acetate or polyvinyl chloride, fatty materials, such as fatty alcohols (for example stearyl alcohol or cetostearyl alcohol), fatty acids (for example stearic acid and palmitic acid), waxes, such as beeswax or carnaubawax and mixtures of these substances.

Very suitable insoluble materials for the restraining phase are the acryl resins known by the trade name Eudragit, for example Eudragit RS or RL; non-ionic polymers insoluble in aqueous media, independent of the pH.

The insoluble material of the restraining phase may be modified by incorporating therein one or more substances which are slowly degradable, especially in the alkaline environment of the intestine. Such a modification may be advantageous, for example, when the solubility of an active ingredient in alkaline medium is lower than in acidic medium. The release rate from the modified restraining phase matrix will then increase in alkaline medium, thereby compensating the decreased solubility.

Suitable degradable ingredients for the restraining phase are, for example, cellulose esters, such as cellulose acetate phthalate, hydroxyalkylcellulose esters, such as hydroxypropylcellulose phthalate (HPCP), or hydroxypropylmethylcellulose phthalate (HPMCP), fatty esters, such as glycerol monostearate. Most preferred as substances modifying the insoluble matrix forming substance of the restraining phase are anionic polyelectrolytes insoluble in acidic aqueous solutions and slowly soluble in neutral or weakly alkaline media, such as Eudragit L and Eudragit S.

The soluble material in the housing phase may be a polyalkylene glycol, for example polyethylene glycol (PEG) having a molecular weight of 500 or more (preferably between 1000 and 6000) or a polyvinylpyrrolidone having a molecular weight of at least 10000 (preferably between 10000 and 360,000).

The penetration rate limiting material in the housing phase may be selected from (a) substances which increase the viscosity, for example starch derivatives, carboxyvinyl polymers (for example Carbopol®), polyethylene glycol (molecular weight of at least 500), polyvinylpyrrolidone (molecular weight at least 10000), hydroxypropylcellulose, hydroxypropylmethylcellulose (HPCM) carboxymethylcellulose, alginates and gelatines;

(b) hydrophobic substances, for example magnesium stearate, calcium-stearate, very pure siliciumdioxide (for example Aerosil R 972);

(c) hydrophilic insoluble polymers constituting a barrier for liquid transport, such as ethylcellulose, and very pure silicium dioxide (for example Aerosil 200 ®).

When the penetration rate limiting material in the housing phase is a carboxyvinyl polymer, such as Carbopol 934 ®, this polymer will form a gel when it comes into contact with an alkaline medium, as in the intestine. This gel will limit the penetration of liquid into the pores occupied by the housing phase. Also in this case it may be advantageous to modify the insoluble matrix material of the restraining phase by incorporating therein one or more of the above-mentioned substances which are degradable in alkaline medium.

Many other excipients commonly used in pharmacy can also be incorporated in the restraining and/or housing phases, such as lactose, talc, Emcompress (an excipient mainly consisting of dicalcium phosphate dihydrate), inulin and other polysaccharides, polyalcohols such as sorbitol, flavours, dyes and lubricating agents. Of course, these additional ingredients should not be used in such amounts in the restraining phase granulate that, in the compressed device, the restraining phase cannot retain its stability as a matrix for the active ingredient.

The restraining phase always contains one or more active ingredients. When the system has to release immediately a part of the active substance, the active material can also be incorporated in other parts, for example in the housing phase or in a rapid release layer on the device. The total amount of active compound(s) in the housing phase and in the restraining phase should not exceed 80% by weight. Preferably, the concentration is not more than 60% by weight.

Although the restraining phase as present in the devices according to the invention is a coherent and continuous phase, it may have been formed from a variety of restraining phase granules each containing a different active ingredient. This may be the case, for example, when a restraining phase granulate formulation suitable for one of the active ingredients is less suitable for another ingredient.

The devices according to the invention may have various forms, and may be e.g. tablets. It will be clear that the devices further may have been subjected to other known pharmaceutical treatments, such as coating or encapsulating so as to adapt them to special requirements, such as protection against atmospheric influences, moisture, gastric fluids etc.

The release of the active ingredient from the restraining phase depends on the total surface area of the restraining phase exposed to the extracting liquid, and on the diffusion characteristics of the restraining phase. When the exposed area is constant, such as in the absence of a housing phase, the rate of release of active ingredient from the restraining phase will decrease gradually due to the fact that the path which the liquid and the active ingredient have to travel inside the restraining phase will become longer. In the devices according to the invention the rate in which the extracting liquid reaches the surface of the restraining phase is determined, in principle, by the penetration characteristics of the housing phase. As the liquid penetrates the housing phase the exposed area of the restraining phase increases. The increase of the exposed area of the restraining phase compensates for the decrease in release rate normally occurring when the exposed area of the restraining phase would be constant. According to the invention the two phases act together so as to give a substantially constant release rate.

In most prior art compositions disintegration plays an important role in the controlled release of active substance. In contrast hereto the devices of the invention are substantially non-disintegrating. Surprisingly, they still show a controlled release pattern. In some cases, disintegration of the devices may still take place, for example when the active substance has been released entirely or for the greater part. This phenomenon is not essential for the release mechanism, however.

By making an appropriate choice of the materials and of their relative amounts, as well as of the size and amount of the particles of the restraining phases, a desired release pattern can be obtained.

It is essential for the devices of the invention that they comprise two continuous phases. This is accomplished by compressing the two granulates in a weight ratio of 30:70 to 70:30. If one of the phases is present in an amount of less than 30 weight percent this phase will not be continuous and the device will not show the desired, substantially constant release rate.

Preferably, the weight ratio of housing phase granulate to restraining phase granulate is 30:70 to 55:45.

Also, the particle size of the granulates shall be 0.4–2.0 mm. Smaller particle sizes result in too fast extraction of the devices and use of particle sizes larger than 2.0 mm have the effect that it is difficult to obtain a coherent restraining phase.

Pharmaceutical formulations according to the invention can provide a zero order release of the active ingredient but, if desired, a formulation can also provide an initial rapid release of part of the active ingredient. When a zero order release is desired it is advantageous that the particles of the restraining phase granulate have a diameter between 0.6 and 1.6 mm. Devices prepared from granulates having these particle sizes therefore are a preferred embodiment of the invention.

The devices according to the invention may contain a great variety of active ingredients. The devices may, for example, be adapted to the necessary concentrations of active substances and to their dissolution properties. Thus, release rates expressed as released percentage of active ingredient content per unit of time will be higher with smaller dimensions of the devices, with smaller particle sizes of the restraining phase granulate, with higher proportions of housing phase granulate in the mixture of granulates, and with lower amounts of insoluble matrix forming substance in the restraining phase. Of course, the release rate also depends on the solubility of the active ingredient, but desirable release rates may be established by varying the above-mentioned parameters of the system.

The invention also includes a process for the preparation of the above-described devices. This process comprises preparing a first granulate which is called the restraining phase granulate, comprising one or more active ingredients dispersed in a matrix comprising one or more substances which are insoluble in the liquid to which the device is intended to release the active ingredient or ingredients, preparing a second granulate which is called the housing phase granulate, comprising a liquid-soluble material and a penetration rate limiting material, one material optionally having both functions, mixing the two granulates having particle sizes of 0.4–2.0 mm, in a weight ratio of 30:70 to 70:30, and compressing the granulate mixture to form a shaped article. Preferably, the two granulates have substantially equal particle sizes.

The restraining phase particles can be obtained as follows. A mixture of drug, insoluble materials and, if desired, excipients, such as lactose, talcum, Emcompress, cetyl alcohol and the like, is wetted in a suitable vessel with a granulation liquid. The granulation liquid may, for example, be a solvent for the insoluble matrix forming material or a solution or dispersion of the matrix forming material in a solvent. The granulation liquid should not leave a matrix of a water-soluble material after evaporation of the solvent, because this would prevent the restraining phase granulate from forming a coherent continuous phase in the device. The wetted mass is continuously stirred and evaporated off until a granuable mass is obtained. After granulation the particles are dried, crushed and screened to obtain the desired particle size. Also dry granulation methods or coating techniques may be used to prepare the granulate of the restraining phase.

The housing phase particles may be prepared by mixing the selected materials and subsequently subjecting the mixture to a dry or wet granulation process. When polyethylene glycols are present in the mixture it is suitable, for instance, to prepare the particles of the housing phase by heating the mixture of the housing phase components above the melting point of the polyethylene glycol and then extruding the mass. Roller-compaction methods are also applicable.

The following examples illustrate the preparation of the devices according to the invention. Unless stated otherwise the release rates were measured in the paddle apparatus according to USP XX at 100 rpm in 0.1N HCl (pH 1.0).

EXAMPLE I

The restraining phase was prepared from the following ingredients:
Eudragit RSPM: 25 g,
Theophylline monohydrate: 44 g,
Cetyl alcohol: 5 g,
Talc: 25 g.

The polymer, the theophylline and the talc were mixed in a suitable vessel. The cetyl alcohol was dissolved in 100 g of chloroform and the solution was added to the powder mixture. The mixture was stirred and the solvent evaporated until a granuable mass was obtained. The mass was extruded and dried and the particles obtained were crushed and screened. Different sieve-fractions were collected and dried for 24 hours at 40° C.

The housing phase was prepared from the following ingredients:
Carbopol 934: 7.5 g,
PEG 6000: 35 g,
Lactose monohydrate: 37 g,
Emcompress: 21,8 g,
Magnesium stearate: 1,8 g.

The PEG 6000 (particle size smaller than 180 micrometer) was mixed with the Carbopol, lactose (<180 micrometer) and the Emcompress (<180 micrometer) in a Turbula mixer. The magnesium stearate was added to the mixture and mixing was continued for another two minutes. The powder mixture was heated to 90° C. until granuable. The mass was extruded, solidified by cooling and comminuted. Different sieve-fractions were collected.

460 parts of the restraining phase were mixed with 530 parts of the housing phase and the mixture was compacted with a compression-force of 10 kN, into cylindrical devices of 990 mg with a diameter of 13 mm, and a height of 5.3 mm. The process was carried out with particle sizes of restraining phase and housing phase granulates of respectively 0.425–0.5 and 0.5–0.85 mm, 0.6–0.71 and 0.5–0.85 mm, 0.71–0.85 and 0.85–1.0 mm and 1.4–1.6 and 1.0–1.6 mm. When measuring the release pattern of the device, it was found that the constant drug release rate is increased when restraining phase particles are smaller.

EXAMPLE II

Following the procedure of Example I and using particle sizes of 0.6–0.71 and 0.5–0.85 mm respectively for restraining phase and housing phase, devices were prepared with varying dimensions. The weights, diameters and heights were respectively 125 mg, 7 and 2.3 mm; 330 mg, 9 and 3.7 mm; 990 mg, 13 and 5.3 mm. It was found that the period of constant drug delivery was extended with increasing dimensions of the devices ($\phi$7 mm: 4 hrs, $\phi$9 mm: 6 hrs, $\phi$13 mm: 8 hrs). See the release curves in FIG. 1. Curve A: diameter 7 mm; curve B: diameter 9 mm; curve C: diameter 13 mm.

EXAMPLE III

The restraining phase was prepared from the following ingredients:
Eudragit RSPM: 15 g
Theophylline monohydrate: 44 g
Talc: 40 g The preparation of the restraining and housing phase granulates and of the tablets was further as described in Example I, except that the granulates were used in varying ratios. The particle sizes of the granules were 1.0–1.6 mm (housing phase) and 1.4–1.6 mm (restraining phase). The ratios of the weights of housing to restraining phase were 530:460; 445:545 and 345:645. The release rate expressed in percentage per hour appeared to decrease when the restraining phase content increased. See FIG. 2 in which curves A, B and C relate to the above-mentioned weight ratios.

EXAMPLE IV

Four different restraining phase granulates were prepared as described in example I from the following ingredients:

|  | R.G. I | R.G. II | R.G. III | R.G. IV |
| --- | --- | --- | --- | --- |
| Eudragit RSPM | 30.0 g | 25.0 g | 15.0 g | 5.0 g |
| Theophylline monohydrate | 44.0 g | 44.0 g | 44.0 g | 44.0 g |
| Cetyl alcohol | 10.0 g | 5.0 g | — | — |
| Talc | 15.0 g | 25.0 g | 40.0 g | — |
| Emcompress ® | — | — | — | 50.0 g |

(RG + restraining phase granulate)

Tablets of 990 mg were prepared of mixtures of each of the granulates with a housing phase granulation as described in Example I with particle sizes of 1.4–1.6 and 1.0–1.6 mm, respectively, and in a ratio of 460 to 530. Preparation of tablets from the mixture was carried out as described in example I. The drug release rate was found to increase in the sequence of preparations with R.G. I, R.G. II, R.G. III and R.G. IV. All of the preparations showed zero-order release.

EXAMPLE V

Three restraining phase granulates were prepared with different amounts of theophylline from the following ingredients:

|  | R.G. V | R.G. VI | R.G. II |
| --- | --- | --- | --- |
| Eudragit RSPM | 20.0 g | 25.0 g | see example IV |
| Theophylline monohydrate | 70.9 g | 22.0 g |  |
| Cetyl alcohol | 5.0 g | 5.0 g |  |
| Talc | 10.0 g | 25.0 g |  |
| Emcompress | — | 20.0 g |  |

Preparation of granules and tablets, particle sizes and ratio of restraining to housing phase were as described in example IV. All of the three preparations showed zero-order release profiles. See FIG. 3, in which curve A relates to RG II, curve B to RG V, and curve C to RG VI.

EXAMPLE VI

Following the procedures of example I, granulates were prepared from the following ingredients:

|  | H.G. I | H.G. II |
| --- | --- | --- |
| Theophylline monohydrate | 21.7 g | — |
| Carbopol 934 | 7.5 g | 7.5 g |
| PEG 6000 | 35.2 g | 36.2 g |
| Lactose | 36.6 g | 58.4 g |

|  | -continued | |
| --- | --- | --- |
| Magnesium stearate | 1.8 g | 1.8 g |

(HG = housing phase granulate)

|  | R.G. I | R.G. II |
| --- | --- | --- |
| Eudragit RSPM | 25.0 g | 25.0 g |
| Theophylline monohydrate | 44.0 g | — |
| Cetyl alcohol | 5.0 g | 5.0 g |
| Talc | 25.0 g | 25.0 g |

Tablets of 990 mg were prepared as described in example I from the following mixtures: HG I+RG II, HG II+RG I.

The following conclusions could be drawn from the results of the release determinations.

Drug release is constant when drug is only incorporated in the restraining phase of the system. Drug release rate is not linear, but decreases with time, when drug is only incorporated in the housing phase (this composition is outside the scope of the invention; it was prepared for comparative purposes).

Further, determinations were made with

A. granulate HGI not compressed to a coherent mass,
B. granulate HGI compressed to a coherent mass,
C. granulate RGI not compressed to a coherent mass,
D. mixture of granulate HGI and RGI, compressed to a coherent mass,
E. granulate RGI compressed to a coherent mass.

Figure 1:
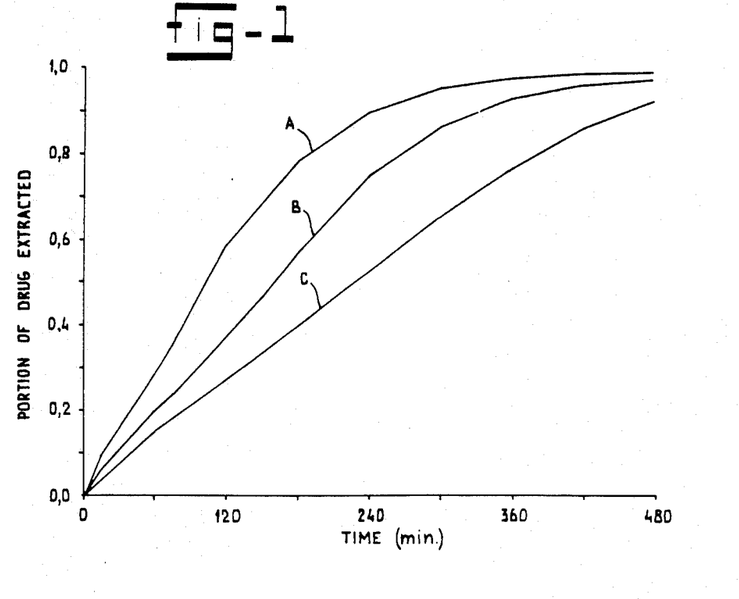
Figure 2:
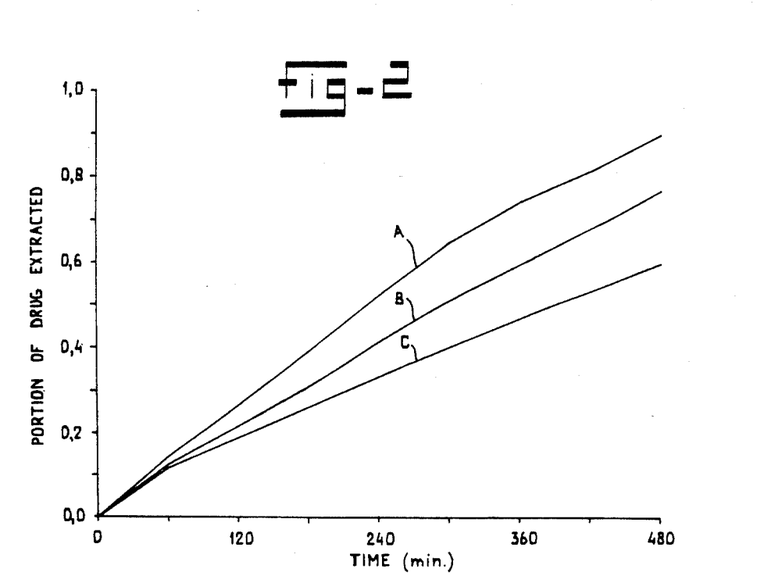
Figure 3:
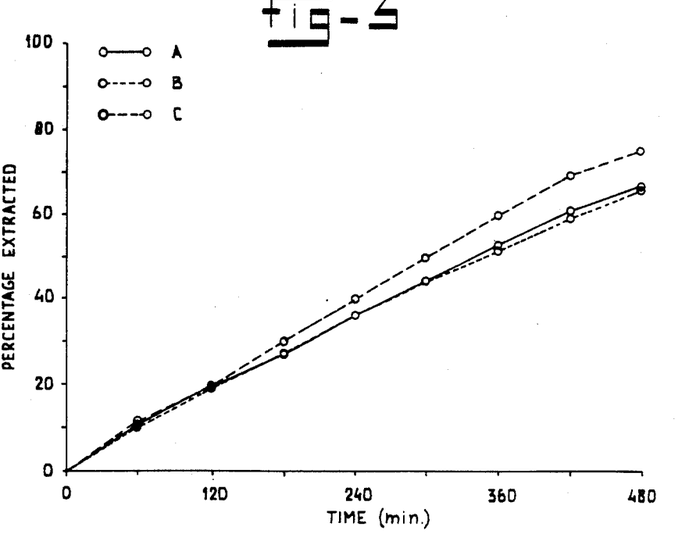
Figure 4:
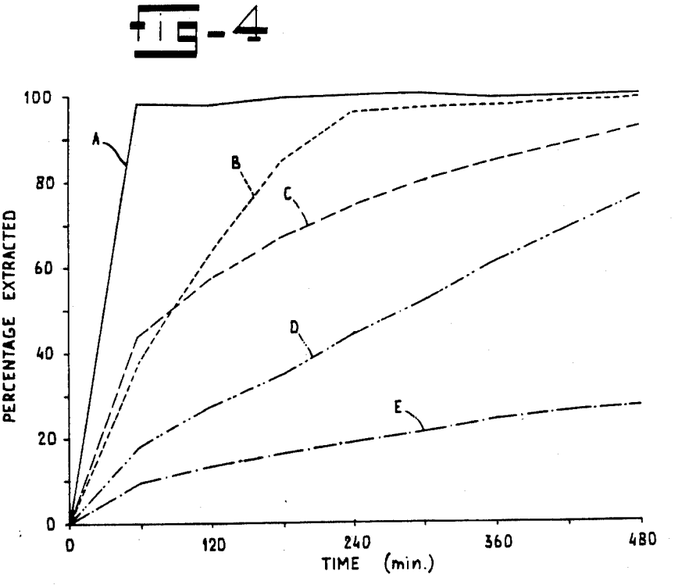

As appears from FIG. 4, none of the compositions appeared to show the desired zero-order release, except the compressed mixture D of HGI and RGI. Initially, an amount of drug is released relatively rapidly and then the drug release rate is constant (curve D of FIG. 4).

EXAMPLE VII

Tablets of 990 mg were prepared of formulation RGIII (particle size 1.4–1.6 mm) according to example IV, and the housing phase granulation according to example I (particle size 1.0–1.6 mm) in a weight ratio of 460 to 530. Drug release studies were performed with the whole tablets and with tablets broken into two or more parts. It was found that drug delivery is only slightly affected by rupture of the device. Consequently, the devices according to the invention appear to be protected against a too rapid release of drug, which might result in toxic or other adverse effects.

EXAMPLE VIII

Restraining phase granules were prepared by mixing the ingredients and then wetting the mixture with chloroform until a pasty mass was formed. The mass was forced through a 2 mm screen and after drying and comminuting the particles of 1.0–1.6 mm were isolated for pressing the tablets.

The housing phase granules were prepared by mixing the ingredients and then melting the mixture at about 90° C. The pasty mass was passed through a 2 mm screen and after solidifying and comminuting the particles of 1.0–1.6 mm were isolated.

The compositions of the granulates are given below:

|  | RG-A | RG-B | RG-C |
| --- | --- | --- | --- |
| Eudragit RLPM | — | — | 25 g |
| Eudragit RSPM | 25 g | 25 g | — |
| Theophylline hydrate | 44 g | 44 g | 44 g |
| Cetyl alcohol | 5 g | — | — |
| Talcum | 25 g | — | 15 g |
| Precirol | — | 30 g | — |
| Cetaceum | — | — | — |
| Lanette O | — | — | 15 g |

|  | HG-A | HG-B |
| --- | --- | --- |
| Theophylline hydrate | 21.7 g | 21.7 g |
| Carbopol 934 | 7.5 g | — |
| PEG 6000 | 35.6 g | 35.6 g |
| Lactose | 36.8 g | 36.6 g |
| Magnesium stearate | 1.8 g | 1.8 g |
| PVP k17PF | — | 7.5 g |
| Carbopol 940 | — | — |

The following mixtures were made and compressed to tablets: HG—A+RG—B, HG—A+RG—C, HG—B+RG—A.

All tablets contained 300 mg of theophylline and consisted of 560 mg of HG and 430 mg of RG. The extraction tests were performed at pH 1.2 (dilute hydrochloric acid) and 6.8 (Sörensen's buffer). The sustained and substantially constant theophylline release was hardly influenced by change of pH.

EXAMPLE IX

The housing phase was prepared by mixing 7.5 g of ethylcellulose; 35 g of PEG 6000 (<180 μm); 35.7 g of lactose (<180 μm) and 20 g of Emcompress (<180 μm). The mixture was heated at ca 90° C. until a moldable mass was formed. The mass was extruded through a Frewitt granulator (screen opening 2.0 mm). The particles of 0.5–0.85 mm were isolated for use in the tablets.

The restraining phase was prepared by mixing 15 g of Eudragit RSPM; 44 g of theophylline monohydrate and 40 g of talc. The mixture was wetted with chloroform until a pasty mass was formed. The mass was forced through a 1.6 mm screen and, after drying, passed through a Frewitt granulator (screen opening 2.0 mm). The particles of 0.6–0.71 mm were isolated.

Tablets with a diameter of 13 mm, consisting of 560 mg of the restraining phase particles and 430 mg of the housing phase particles were prepared. The tablets contained ca. 240 mg of theophylline monohydrate.

Figure 5:
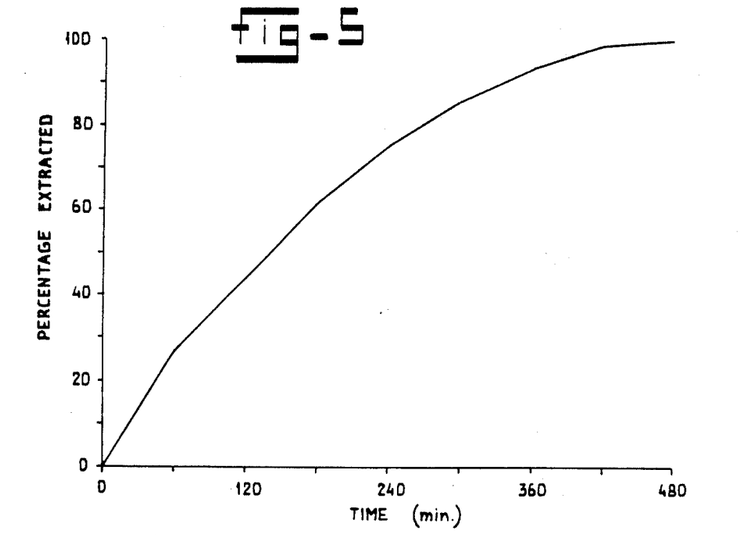

The release pattern is shown in FIG. 5.

EXAMPLE X

This example relates to the use of the wet granulation method.

A. Preparation of the housing phase granules (HG)

10.8 g of theophylline monohydrate; 3.8 g of Carbopol; 17.6 g of PEG 6000 and 18.4 g of lactose were mixed together for ca. 10 minutes. Then 0.9 g of magnesium stearate was added and after mixing for another 2 minutes, dichloromethane was added until a pasty mass was formed. The mass was forced through a 2 mm screen and, after drying, the particles of 1.0 to 1.6 mm were isolated by sieving.

B. Preparation of the restraining phase granules (RG)

12.5 g of Eudragit RSPM; 22 g of theophylline monohydrate and 12.5 g of talcum were mixed for ca. 10 minutes. Then the mixture was blended with a solution of 2.5 g of cetyl alcohol in 50 g of dichloromethane. After evaporation of a part of the dichloromethane a pasty mass was formed which was pressed through a 2 mm screen. After drying, the particles of 1.0 to 1.6 mm were isolated by sieving.

C. Preparation of the tablets 460 parts of the RG granulate were thoroughly mixed with 530 parts of the HG granulate. Tablets of 990 mg were pressed from the mixture on a Corsch tablet press. The tablets contained ca. 300 mg of theophylline. Extraction tests were performed at pH 1.2 (dilute hydrochloric acid) and 6.8 (Sörensen's buffer). A small amount of the drug is released relatively quickly, and then a constant rate is established.

EXAMPLE XI

The following ingredients were thoroughly mixed: 12.5 g of Eudragit RSPM; 32.8 g of theophylline monohydrate; 2.5 g of cetyl alcohol; 12.5 g of talc; 3.8 g of Carbopol; 17.6 g of PEG 6000; 18.4 g of lactose and 0.9 g of magnesium stearate. The mixture was divided into two portions A and B. Portion A was directly compressed to tablets of 990 mg containing ca. 300 mg of theophylline. Mixture B was granulated by melting at 90° C. and then pressing the pasty mass through a 2 mm screen. After solidifying, the particles of 1.0–1.6 mm were isolated by sieving and compressed into tablets of 990 mg. The dissolution rates of the tablets were compared with that of the granules. The release rates of tablets of mixture A were measured at pH 6.8 (Sörensen's buffer) and 1.2; the release rates of granules and tablets of mixture B were measured at pH 1.2.

Figure 6:
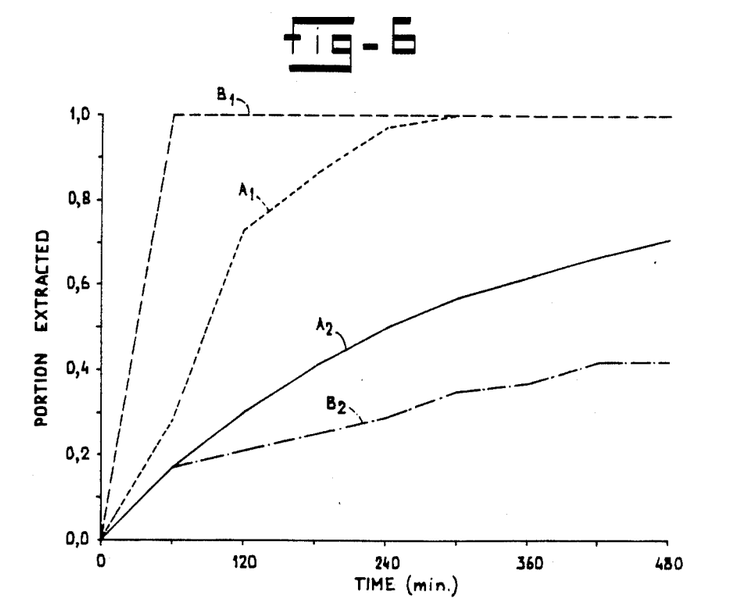

The results of these tests are given in FIG. 6. Curve $A_1$ relates to tablet A at pH 6.8; curve $A_2$ relates to tablet A at pH 1.2; curve $B_1$ relates to granulate B at pH 6.8; and curve $B_2$ relates to tablet B at pH 1.2.

The preparations described in this example are outside the scope of the invention. The directly compressed tablets showed a non-linear dissolution profile, and the difference between the release at pH 1.2 and 6.8 was considerable.

The granules of the total mixture rapidly release the substance and the tablets prepared of these granules show a very slow release.

EXAMPLE XII

A. Preparation of the restraining phase granules with Eudragit RSPM (RG)

A mixture of 53.6 g of amoxycillin trihydrate; 25 g of Eudragit RSPM and 23.3 g of talc was wetted with a solution of 5 g of cetyl alcohol in 100 ml of chloroform. The mixture was stirred until a pasty mass was formed. The mass was pressed through a 2 mm screen. After drying, the particles of 1.0–1.6 mm were isolated.

B. Preparation of the housing phase granules (HG)

A mixture of 15 g of Carbopol 934; 26.5 g of amoxycillin trihydrate; 30 g of PEG 6000; 1.8 g of magnesium stearate and 28 g of Emcompress was heated at ca. 90° C. until granuable. The pasty mass was pressed through a 2 mm screen. After solidifying, the particles of 1.0–1.6 mm were isolated.

Figure 7:
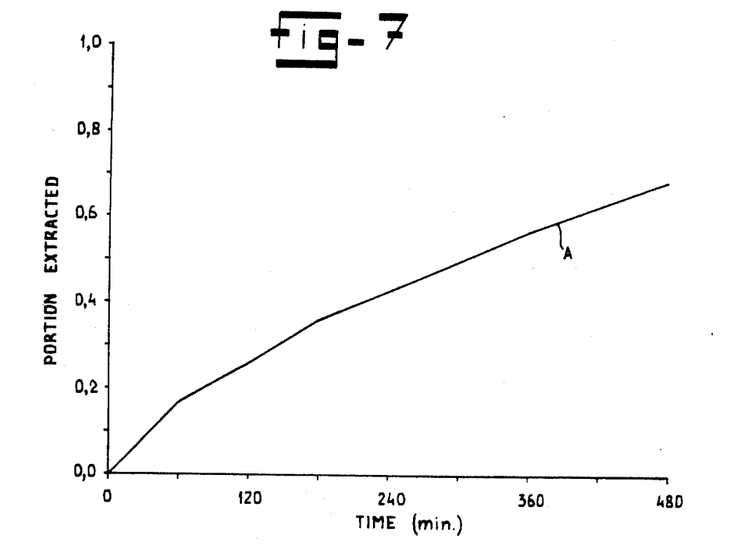

Tablets with a diameter of 13 mm consisting of 530 mg of HG and 460 mg of RG were compressed with a force of 20 kN. The tablets contained ca. 370 mg of amoxycillin trihydrate. The release profile in acidic medium (pH 1) is given in FIG. 7.

EXAMPLE XIII

Preparation of the housing phase

Dichloromethane was added to a mixture of 10.8 g of coffein; 3.8 g of Carbopol 934; 17.6 g of PEG 6000; 18.4 g of lactose and 0.9 g of magnesium stearate until a pasty mass was formed. The mass was forced through a 2 mm screen. After drying, the particles of 1.0–1.6 mm were isolated.

Preparation of the restraining phase

A solution of 2.5 g of cetyl alcohol in 50 ml of dichloromethane was added to a mixture of 12.5 g of Eudragit RSPM; 22 g of coffein and 12.5 g of talcum. The pasty mass was forced through a 2 mm screen. After drying, the particles of 1.0–1.6 mm were isolated.

Tablets consisting of 310 mg of the housing phase granules and 672 mg of the restraining phase granules were pressed. The tablets contained ca. 360 mg of coffein. The extraction rates were determined at pH 1.2 and 6.8 (Sörensen buffer).

Figure 8:
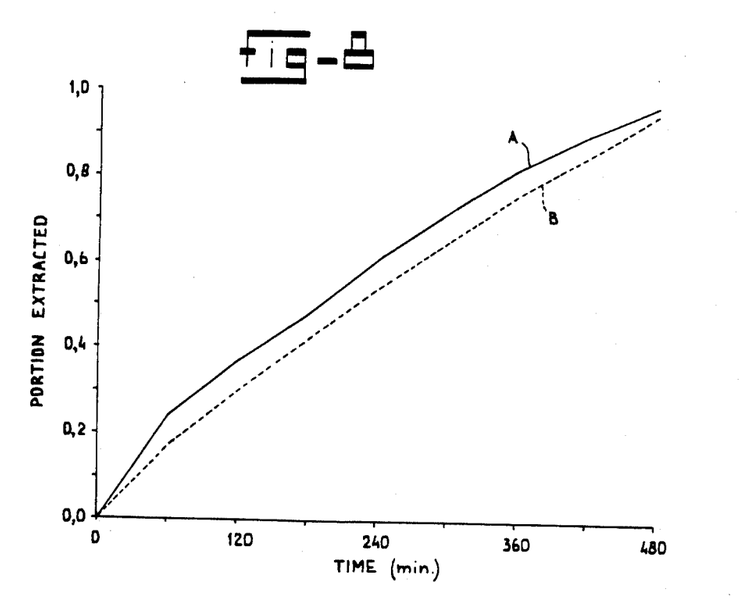

FIG. 8 shows the release profiles. Profile A at pH 1.2, and profile B at pH 6.8.

EXAMPLE XIV

The restraining phase granules were prepared by mixing 12.5 g of Eudragit RSPM; 11 g of salicylic acid; 12.5 g of talcum and 16.5 g of lactose. The mixture was blended to a pasty mass by adding a solution of 2.5 g of cetyl alcohol in 50 g of dichloromethane. The mass was forced through a 2 mm screen. After drying, the particles of 1.0–1.6 mm were isolated.

The housing phase granules were prepared by mixing 25 g of salicylic acid; 5 g of Carbopol 934; 17.6 g of PEG 6000 and 10 g of lactose. By addition of dichloromethane a pasty mass was formed which was pressed through a 2 mm screen. After drying, the particles of 1.0–1.6 mm were isolated.

Tablets consisting of 500 mg of the restraining phase granules and 460 mg of the housing phase were pressed on a Corsch tablet press ($\phi$13 mm). The dissolution rates were measured at pH 1.2 and 6.8 (Sörensen buffer). An equally retarded release rate is found in both of the media.

EXAMPLE XV

Tablets having a diameter of 13 mm were prepared from a mixture of 643 mg RGIII (see example IV) with 347 mg of HGIII, the composition of which is given below, on the one side, and from 643 mg RGII (see example IV) and 347 mg HGIII on the other side. The granulates RGIII and RGII had a particle size of 0.6–0.71 mm, and the granulate HGIII had a particle size of 0.5–0.85 mm. The preparation of the housing phase was effected by means of the melting method as described in example I for the housing phase. The compression force used for the preparation of the tablets was 29 kN.

The composition of HGIII was as follows:
PVP K90: 50.00 g,
PEG 6000: 36.20 g,
Emcompress: 13.80 g.

Figure 9:
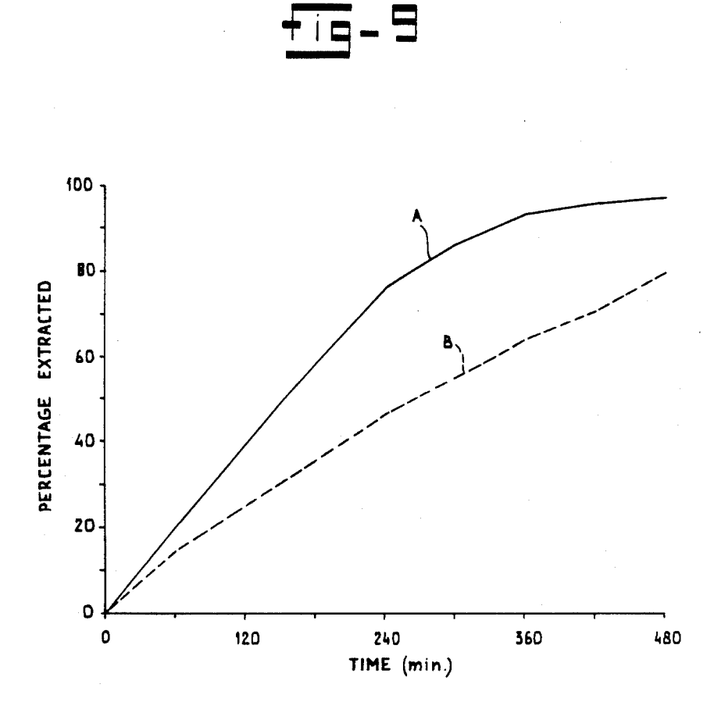

The results of the extraction tests are given in FIG. 9. Curve A therein relates to the combination of RGIII with HGIII, and curve B relates to the combination of RGII with HGIII.

When the tablets had been leached out completely a coherent, porous residue remained which was resistant to mechanical stress applied to the tablets during the extraction test. It is to be assumed that the tablets will not disintegrate in the gastro-intestinal tract either.

EXAMPLE XVI

This example illustrates the modification of the insoluble matrix material, in this case Eudragit RSPM, of the restraining phase by incorporating therein a material which is soluble in neutral or alkaline medium, in this case Eudragit L.

A restraining phase granulate was prepared from the following ingredients by using the method described in Example I with the difference that acetone instead of chloroform was used as the granulation liquid. The granulate used for making the tablets had a particle size of 1.4–1.6 mm.

Restraining phase

Eudragit RSPM: 5 g,
Eudragit L: 20 g,
Theophylline monohydrate: 44 g,
Talc: 30 g.

A housing phase granulate was prepared as described in Example I from the following ingredients. Particle size: 1.0–1.6 mm.

Housing phase

Carbopol 934: 7.5 g,
PEG 6000: 92.5 g.

Cylindrical tablets were prepared from a mixture of 460 mg of the restraining phase and 530 mg of the housing phase. Compression force: 10 kN.

The drug release rate of the tablets was dependent on the pH. The release rate was higher in phosphate buffer pH 6.8 than in 0.1N HCl (pH 1.0).

It will be apparent that the amounts and weight ratios of Eudragit RSPM and Eudragit L in the restraining phase granulate may be varied so as to obtain other pH dependent or a pH independent release profile.

We claim:

1. A shaped article for the controlled release of at least one active ingredient to a liquid, comprising:
    (a) a restraining phase granulate comprising at least one active ingredient dispersed in a matrix comprising at least one material insoluble in the liquid; and
    (b) a housing phase granulate comprising a material soluble in the liquid and a penetration rate limiting material;

said shaped article formed by compressing a mixture of particles of size about 0.4 to 2 mm, of said restraining phase granulate and said housing phase granulate in a weight ratio of 30:70 to 70:30 to form a shaped article in which both restraining and housing phases are substantially continuous.

2. Article according to claim 1, characterized in that the housing phase also comprises one or more active substances.

3. Article according to claim 1 or 2, characterized in that it is intended for use in human or veterinary medicine.

4. Article according to claim 3, characterized in that it is intended for oral administration.

5. Article according to claim 1, characterized in that the weight ratio of housing phase granulate to restraining phase granulate is 30:70 to 55:45.

6. Article according to claim 1 or 2, characterized in that the amount of active ingredient in the device is not more than 80% by weight.

7. Article according to claim 6, characterized in that the amount of active ingredient in the device is not more than 60% by weight.

8. Article according to claim 1, characterized in that the liquid-soluble material in the housing phase granulate is a polyalkylene glycol having a molecular weight of at least 500 or a polyvinylpyrrolidone having a molecular weight of at least 10000.

9. Article according to claim 8, characterized in that the material is a polyethylene glycol having a molecular weight of at least 500.

10. Article according to claim 8, wherein said polyalkylene glycol has a molecular weight between 1000 and 6000.

11. Article according to claim 9, wherein said polyethylene glycol has a molecular weight between 1000 and 6000.

12. Article according to claim 1, characterized in that the penetration rate limiting material in the housing phase granulate is selected from the group consisting of (a) substances increasing the viscosity, (b) hydrophobic substances and (c) hydrophilic insoluble polyers constituting a barrier for liquid transport.

13. Article according to claim 12, characterized in that the penetration rate limiting material is a substance increasing the viscosity and is selected from the group consisting of carboxyvinyl polymers starch derivatives, polyethylene glycols having a molecular weight of at least 500, polyvinylpyrrolidones having a molecular weight of at least 10000, hydroxypropylcellulose, hydroxypropylmethylcellulose, carboxymethylcellulose, alginates and gelatines.

14. Article according to claim 12, characterized in that the penetration rate limiting material is a hydrophobic substance selected from the group consisting of magnesium stearate, calcium stearate and very pure silicium dioxide.

15. Article according to claim 12, characterized in that the penetration rate limiting material is an insoluble polymer constituting a barrier for liquid transport and is selected from the group consisting of ethylcellulose, and very pure silicium dioxide.

16. Article according to claim 1, characterized in that the insoluble material in the restraining phase granulate is selected from the group consisting of acrylic resins, cellulose derivatives, polymers, fatty materials and waxes.

17. Article according to claim 16, characterized in that the insoluble material is an acrylic resin.

18. Article according to claim 16, characterized in that the insoluble material is an alkylcellulose.

19. Article according to claim 18, wherein the insoluble material is ethyl cellulose.

20. Article according to claim 16, characterized in that the insoluble material is a polymer selected from the group consisting of polyvinyl acetate and polyvinyl chloride.

21. Article according to claim 16, characterized in that the insoluble material is a fatty material selected from the group consisting of fatty alcohols and fatty acids.

22. Article according to claim 21, wherein the fatty alcohol is stearyl alcohol or cetostearyl alcohol and the fatty acid is stearic acid or palmitic acid.

23. Article according to claim 16, characterized in that the insoluble material is a wax selected from the group consisting of beeswax or carnabauwax.

24. Article according to claim 16, wherein said insoluble material is polyvinyl acetate or polyvinyl chloride.

25. Article according to claim 16, characterized in that the insoluble material of the restraining phase granulate has been modified by incorporating therein a substance which is degradable in neutral or alkaline medium.

26. Article according to claim 25, characterized in that the degradable substance is selected from the group consisting of cellulose esters, hydroxyalkylcellulose esters, fatty esters and anionic polyelectrolytes insoluble in acidic aqueous solutions and slowly soluble in neutral or weakly alkaline media.

27. Article according to claim 26, characterized in that the anionic electrolyte insoluble in acidic aqueous solutions and slowly soluble in neutral or weakly alkaline media is Eudragit L or Eudragit S.

28. Article according to claim 26, wherein the cellulose ester is cellulose acetate phthalate, the hydroxyalkylcellulose ester is hydroxypropylcellulose phthalate or hydroxypropylmethylcellulose phthalate, and the fatty ester is glycerol monostearate.

29. Article according to claim 1, characterized in that the granulates have substantially equal particle sizes.

30. Article according to claim 1, wherein the material soluble in the liquid and the penetration rate limiting material are the same material.

31. Process for preparing a device for the controlled release of one or more active ingredients to a liquid, which comprises preparing a first granulate which is called the restraining phase granulate, comprising one or more active ingredients dispersed in a matrix comprising one or more substances which are insoluble in the liquid to which the device is intended to release the active ingredient or ingredients, preparing a second granulate which is called the housing phase granulate, comprising a liquid-soluble material and a penetration rate limiting material, mixing the two granulates having particle sizes of 0.4–2.0 mm, in a weight ratio of 30:70 to 70:30, and compressing the granulate mixture to form a shaped article.

32. Process according to claim 31, characterized in that the particles of both granulates have substantially equal particle sizes.

33. Process according to claim 31, wherein the liquid-soluble material and the penetration rate limiting material are the same material.

* * * * *